(12) United States Patent
Megerian et al.

(10) Patent No.: US 11,763,946 B2
(45) Date of Patent: Sep. 19, 2023

(54) GRAPH-BASED PREDICTIVE INFERENCE

(71) Applicant: Optum, Inc., Minnetonka, MN (US)

(72) Inventors: Mark Gregory Megerian, Rochester, MN (US); Edward Sverdlin, Edina, MN (US); Jonathan Lawrence Herke, Maple Grove, MN (US); Brent Mosier, Boston, MA (US); Andrew Waiming Han, Waltham, MA (US)

(73) Assignee: Optum, Inc., Minnetonka, MN (US)

( * ) Notice: Subject to any disclaimer, the term of this patent is extended or adjusted under 35 U.S.C. 154(b) by 447 days.

(21) Appl. No.: 16/803,465

(22) Filed: Feb. 27, 2020

(65) Prior Publication Data

US 2021/0272693 A1  Sep. 2, 2021

(51) Int. Cl.
*G16H 50/20* (2018.01)
*G06F 17/18* (2006.01)
*G06F 9/54* (2006.01)
*G16H 20/10* (2018.01)

(52) U.S. Cl.
CPC .............. *G16H 50/20* (2018.01); *G06F 9/54* (2013.01); *G06F 17/18* (2013.01); *G16H 20/10* (2018.01)

(58) Field of Classification Search
CPC ........ G16H 50/20; G16H 20/10; G16H 50/70; G16H 70/40; G06F 9/54; G06F 17/18
See application file for complete search history.

(56) References Cited

U.S. PATENT DOCUMENTS

| | | | |
|---|---|---|---|
| 11,298,477 B2 * | 4/2022 | Davidson | A61P 25/04 |
| 2002/0010595 A1 * | 1/2002 | Kapp | G16H 70/40 705/2 |
| 2002/0165762 A1 * | 11/2002 | Goldman | G16H 10/20 703/11 |
| 2005/0100926 A1 * | 5/2005 | Chen | C12Q 1/6881 514/217 |

(Continued)

FOREIGN PATENT DOCUMENTS

CN   109064294 A   12/2018

OTHER PUBLICATIONS

E. Andrei, V., Cristian, D., Marineci, C. D., & Simona, N. (2020). The development of a scoring and ranking strategy for a patient-tailored adverse drug reaction prediction in polypharmacy. Scientific Reports (Nature Publisher Group), 10(1) (Year: 2020).*

*Primary Examiner* — Amber A Misiaszek
(74) *Attorney, Agent, or Firm* — Alston & Bird LLP

(57) ABSTRACT

There is a need to perform predictive inference to predict likely adverse events of a drug regimen consisting of multiple drugs. In one example, a method includes determining, based at least in part on a graph-based predictive database, one or more predictive categories for each patient node of a plurality of patient nodes; determining, based at least in part on each one or more predictive categories for a patient node and each of one or more patient attribute nodes for a patient node, a related patient cohort for the primary patient node, wherein the related patient cohort comprises the primary patient node and one or more related patient nodes; determining, based at least in part on one or more intake relationships for each patient node in the related patient cohort, a first related drug profile for the primary patient node; and generating a first prediction interface based at least in part on the first related drug profile.

17 Claims, 14 Drawing Sheets

(56) References Cited

U.S. PATENT DOCUMENTS

| | | | |
|---|---|---|---|
| 2006/0089592 A1 | 4/2006 | Kadhiresan et al. | |
| 2013/0173305 A1* | 7/2013 | Hyde | G16H 20/30 |
| | | | 705/3 |
| 2013/0179091 A1 | 7/2013 | Jackson et al. | |
| 2013/0179375 A1 | 7/2013 | Tatonetti et al. | |
| 2015/0161331 A1* | 6/2015 | Oleynik | G16H 10/60 |
| | | | 705/3 |
| 2016/0335412 A1 | 11/2016 | Tucker et al. | |
| 2016/0342742 A1* | 11/2016 | Chapman-McQuiston | |
| | | | G16H 10/60 |
| 2018/0330824 A1 | 11/2018 | Athey et al. | |
| 2019/0282115 A1* | 9/2019 | Volpe | G16H 50/30 |
| 2021/0202103 A1* | 7/2021 | Bostic | G16H 50/80 |

* cited by examiner

| Patient: Anderson, Fred | DIAGNOSIS CODES | GROUPING | SELECTED FOR ANALYSIS |
|---|---|---|---|
| Male, age 62, Race: Caucasian | | | |
| | Malignant neoplasm of right lung lobe | LUNG CANCER | x |
| | Malignant neoplasm of left lung lobe | LUNG CANCER | x |
| | Elevated blood pressure | HYPERTENSION | x |
| | Fracture of right ulna | BROKEN ARM | |

Select Drugs Based on the Related Patient Cohort and the
Prescribed Drugs for the Patient
1101

Retrieve a First Adverse Event Occurrence Profile
1102

Determine A Related Primary Adverse Event Occurrence Profile
1103

GRAPH-BASED PREDICTIVE INFERENCE

BACKGROUND

Various embodiments of the present invention address technical challenges related to performing predictive inferences in complex prediction domains. Various complex-domain prediction tasks present substantial efficiency and reliability challenges because of the complexity of their respective input and output spaces. Various embodiments of the present invention address the shortcomings of the noted complex-domain prediction systems and disclose various techniques for efficiently and reliably performing complex-domain predictive inferences.

BRIEF SUMMARY

In general, embodiments of the present invention provide methods, apparatus, systems, computing devices, computing entities, and/or the like for performing/executing a graph-based medical prediction for a medical-need scenario. Certain embodiments utilize systems, methods, and computer program products that performing/executing a medical prediction for a medical-need scenario using a graph-based predictive database comprising relationships between patient nodes, claim nodes, diagnosis code nodes, drug nodes, and patient attribute nodes.

In accordance with one aspect, a method is provided. In one embodiment, the method comprises determining, based at least in part on a graph-based predictive database, one or more predictive categories for each patient node of the plurality of patient nodes, wherein the graph-based predictive database comprises one or more historical relationships between the plurality of patient nodes and one or more claim nodes, one or more encoding relationships between the one or more claim nodes and one or more diagnosis code nodes, one or more intake relationships between the plurality of patient nodes and one or more drug nodes, and one or more patient attribute nodes for each patient node of the plurality of patient nodes; determining, based at least in part on each one or more predictive categories for a patient node of the plurality of patient nodes and each one or more patient attribute nodes for a patient node of the plurality of patient nodes, a related patient cohort for the primary patient node, wherein the related patient cohort comprises the primary patient node and one or more related patient nodes of the plurality of patient nodes associated with the primary patient node; determining, based at least in part on the one or more intake relationships for each patient node in the related patient cohort, a first related drug profile for the primary patient node; and generating a first prediction interface based at least in part on the first related drug profile.

In accordance with another aspect, a computer program product for performing a graph-based medical prediction for a medical-need scenario is provided. The computer program product for performing a graph-based medical prediction for a medical-need scenario comprises at least one non-transitory computer-readable storage medium having computer-readable program code portions stored therein, the computer-readable program code portions configured to: determine, based at least in part on a graph-based predictive database, one or more predictive categories for each patient node of the plurality of patient nodes, wherein the graph-based predictive database comprises one or more historical relationships between the plurality of patient nodes and one or more claim nodes, one or more encoding relationships between the one or more claim nodes and one or more diagnosis code nodes, one or more intake relationships between the plurality of patient nodes and one or more drug nodes, and one or more patient attribute nodes for each patient node of the plurality of patient nodes; determine, based at least in part on each one or more predictive categories for a patient node of the plurality of patient nodes and each one or more patient attribute nodes for a patient node of the plurality of patient nodes, a related patient cohort for the primary patient node, wherein the related patient cohort comprises the primary patient node and one or more related patient nodes of the plurality of patient nodes associated with the primary patient node; determine, based at least in part on the one or more intake relationships for each patient node in the related patient cohort, a first related drug profile for the primary patient node; and generate a first prediction interface based at least in part on the first related drug profile.

In accordance with another aspect, an apparatus for performing a graph-based medical prediction for a medical-need scenario is provided. The apparatus for performing a graph-based medical prediction for a medical-need scenario comprises at least one processor and at least one memory including program code, the at least one memory and the program code configured to, with the processor, cause the apparatus to at least: determine, based at least in part on a graph-based predictive database, one or more predictive categories for each patient node of the plurality of patient nodes, wherein the graph-based predictive database comprises one or more historical relationships between the plurality of patient nodes and one or more claim nodes, one or more encoding relationships between the one or more claim nodes and one or more diagnosis code nodes, one or more intake relationships between the plurality of patient nodes and one or more drug nodes, and one or more patient attribute nodes for each patient node of the plurality of patient nodes; determine, based at least in part on each one or more predictive categories for a patient node of the plurality of patient nodes and each one or more patient attribute nodes for a patient node of the plurality of patient nodes, a related patient cohort for the primary patient node, wherein the related patient cohort comprises the primary patient node and one or more related patient nodes of the plurality of patient nodes associated with the primary patient node; determine, based at least in part on the one or more intake relationships for each patient node in the related patient cohort, a first related drug profile for the primary patient node; and generate a first prediction interface based at least in part on the first related drug profile.

BRIEF DESCRIPTION OF THE DRAWINGS

Figure 1:
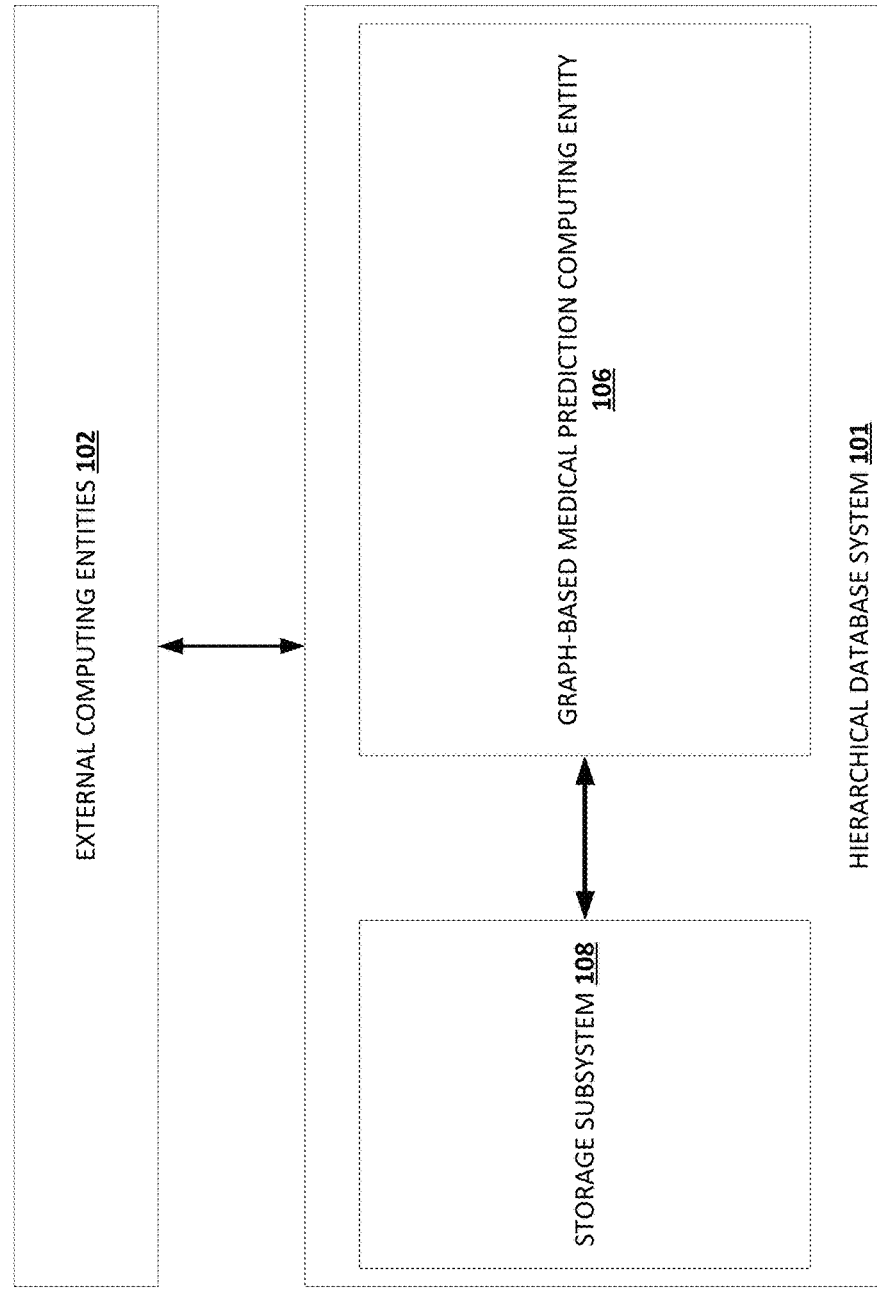

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
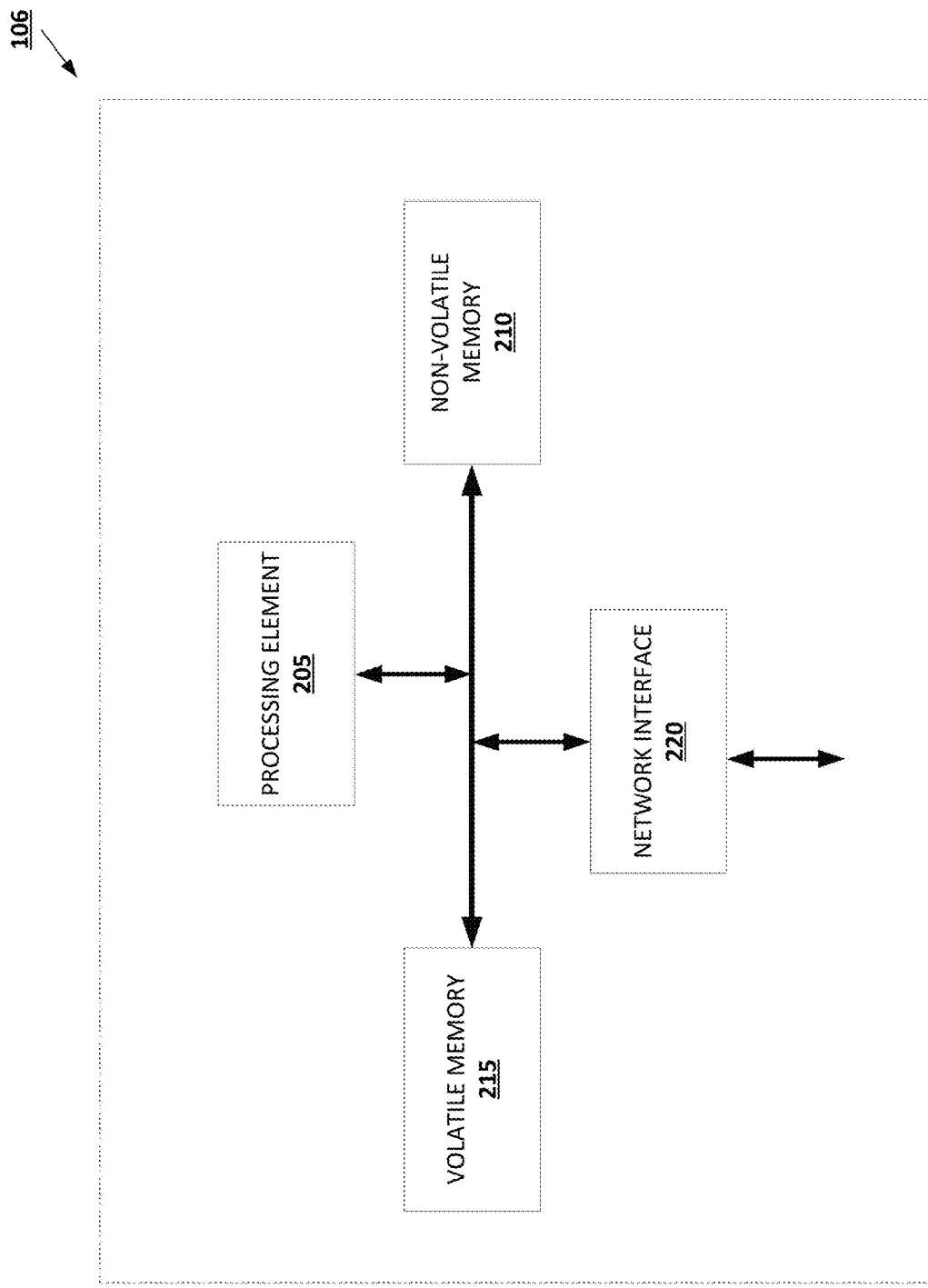

FIG. 2 provides an example graph-based medical prediction computing entity, in accordance with some embodiments discussed herein.

Figure 3:
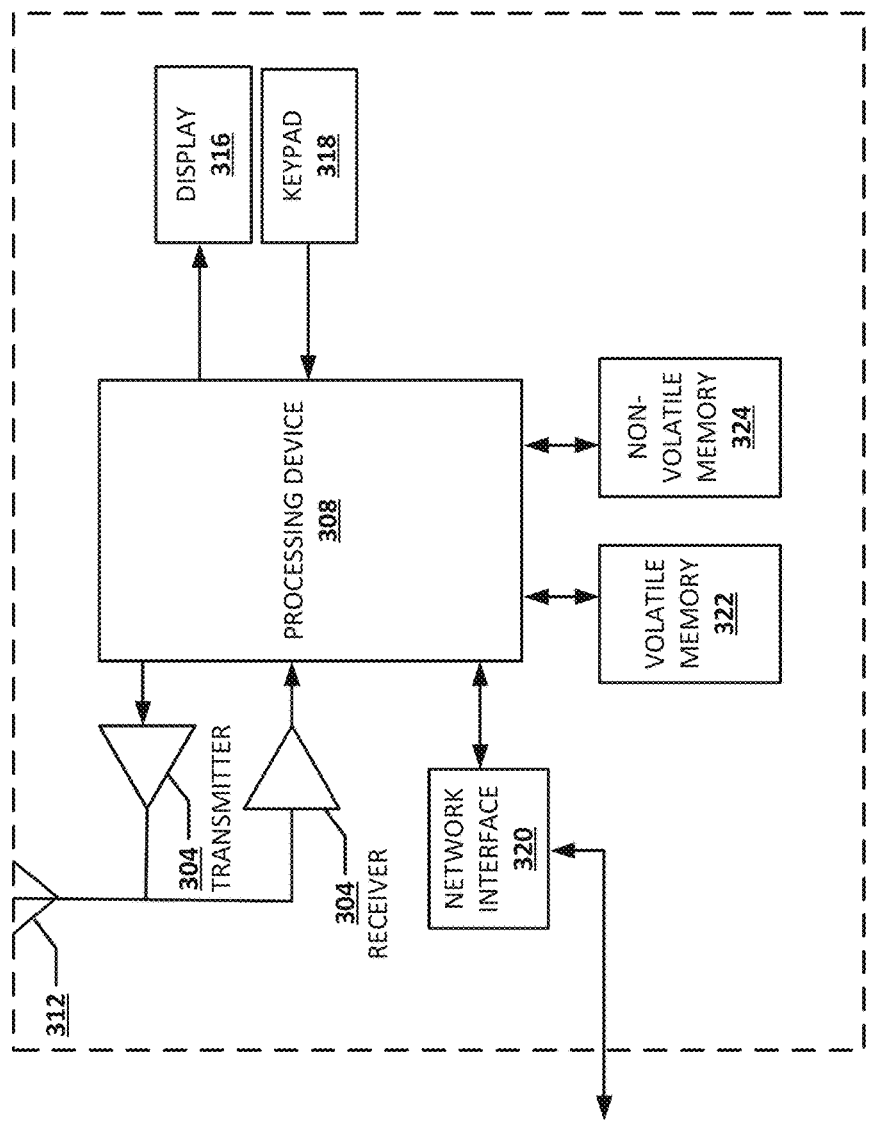

FIG. 3 provides an example external computing entity, in accordance with some embodiments discussed herein.

Figure 4:
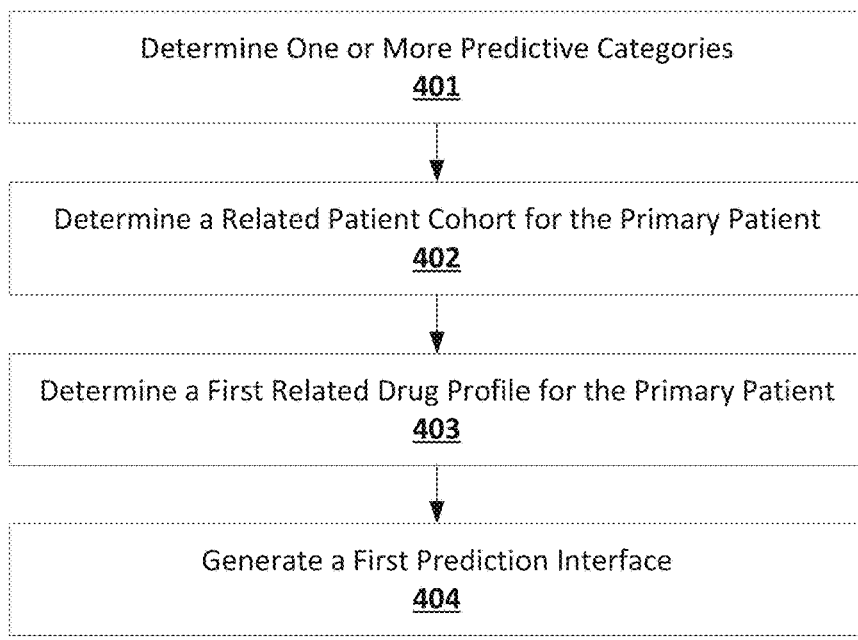

FIG. 4 provides an example process for performing/executing a graph-based medical prediction for a medical medical-need scenario, in accordance with some embodiments discussed herein.

Figure 5:
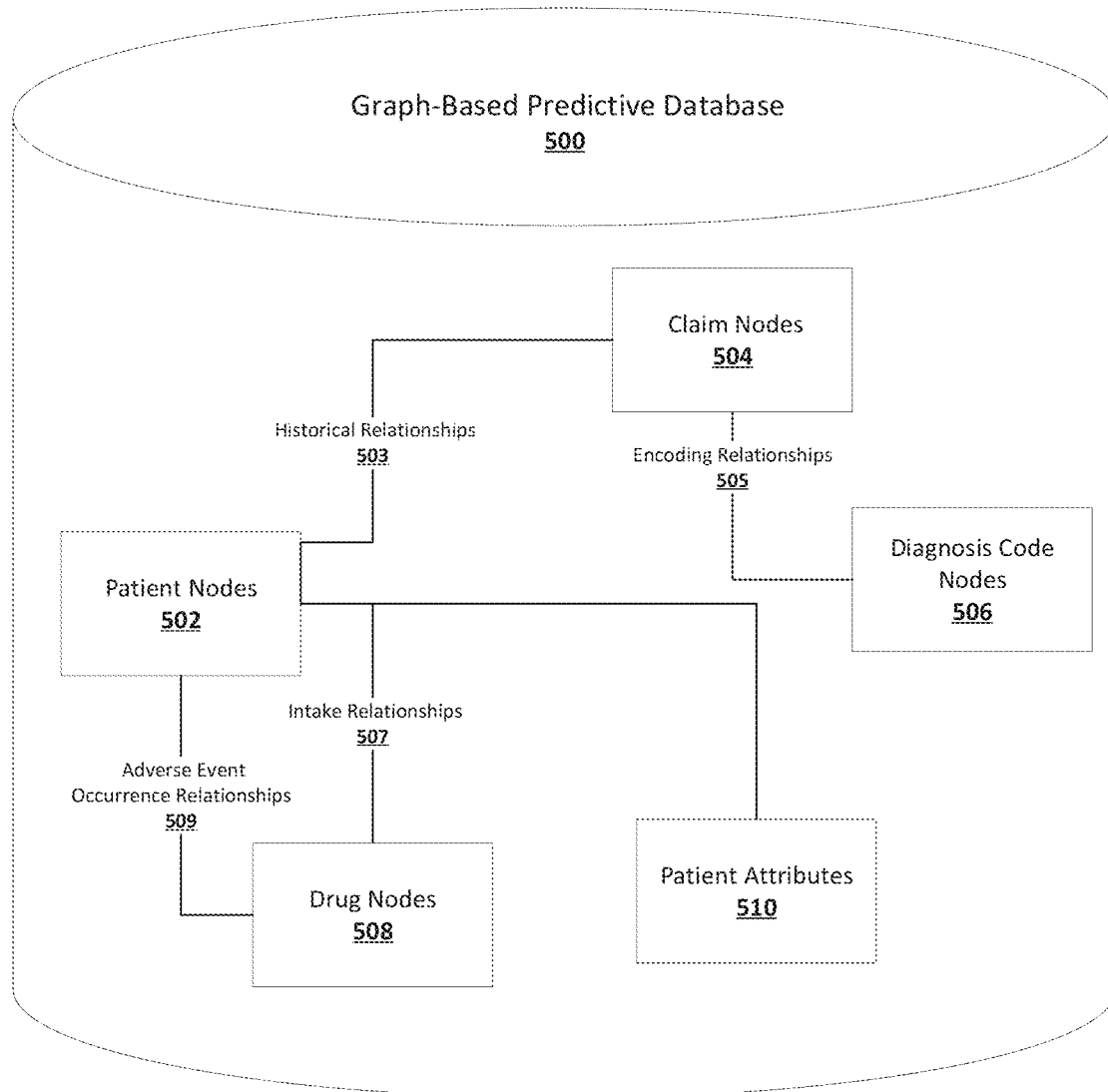

FIG. 5 provides an example of a graph-based predictive database, in accordance with some embodiments discussed herein.

Figure 6:
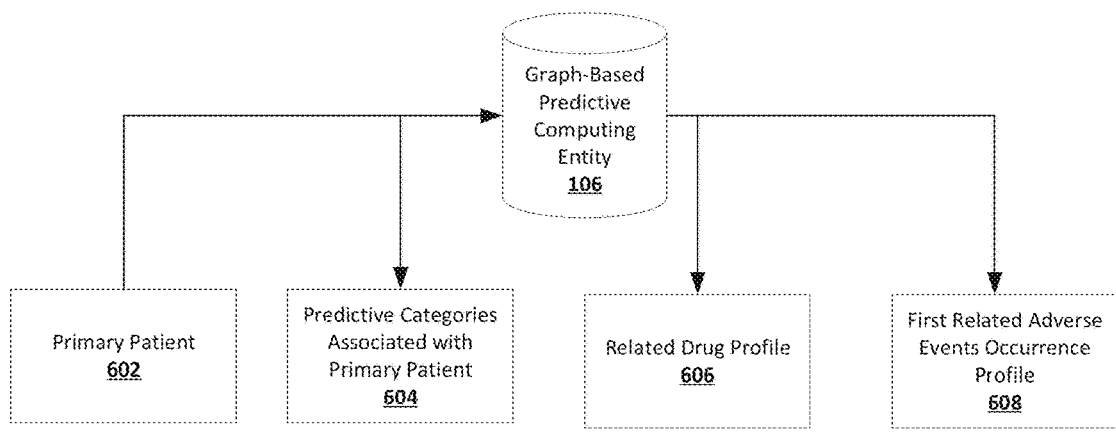

FIG. 6 is an operational flow diagram of an example process for determining a related adverse event-occurrence profile, in accordance with some embodiments discussed herein.

Figure 7:
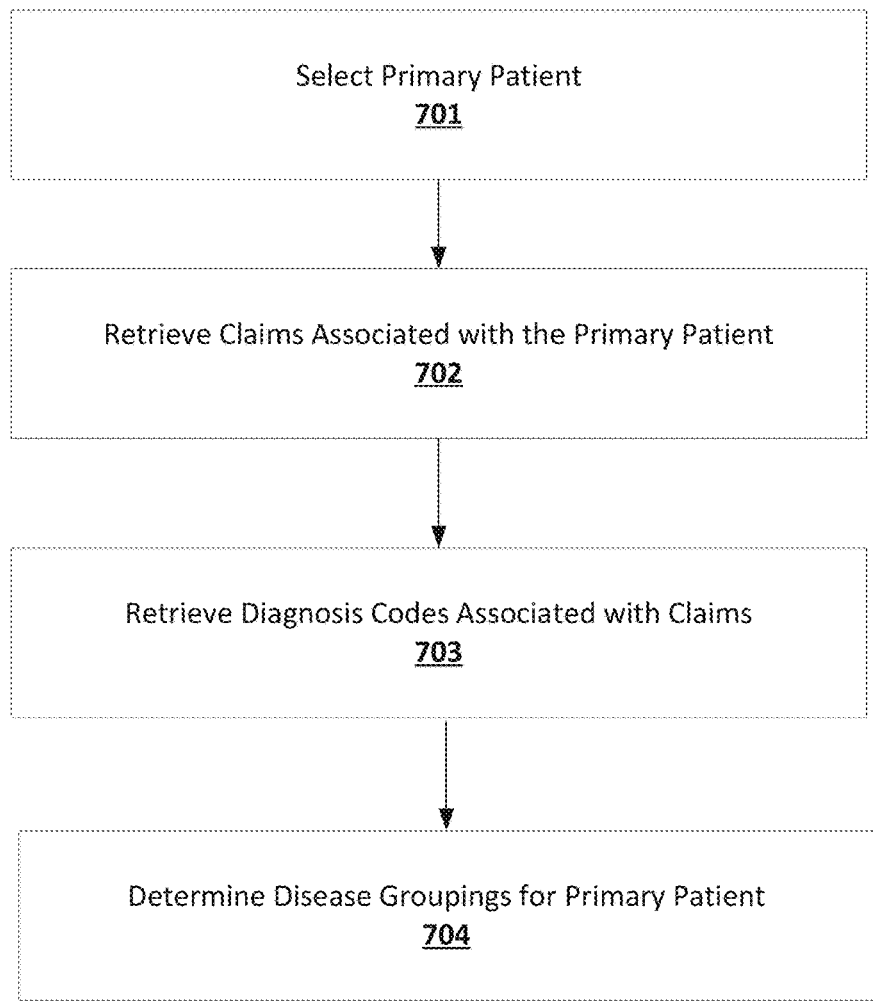

FIG. 7 provides an example process for determining one or more diagnosis grouping for the primary patient, in accordance with some embodiments discussed herein.

FIG. 8 is an operational example of a graph-based medical prediction for a medical-need scenario associated with a primary patient, in accordance with some embodiments discussed herein.

Figure 9:
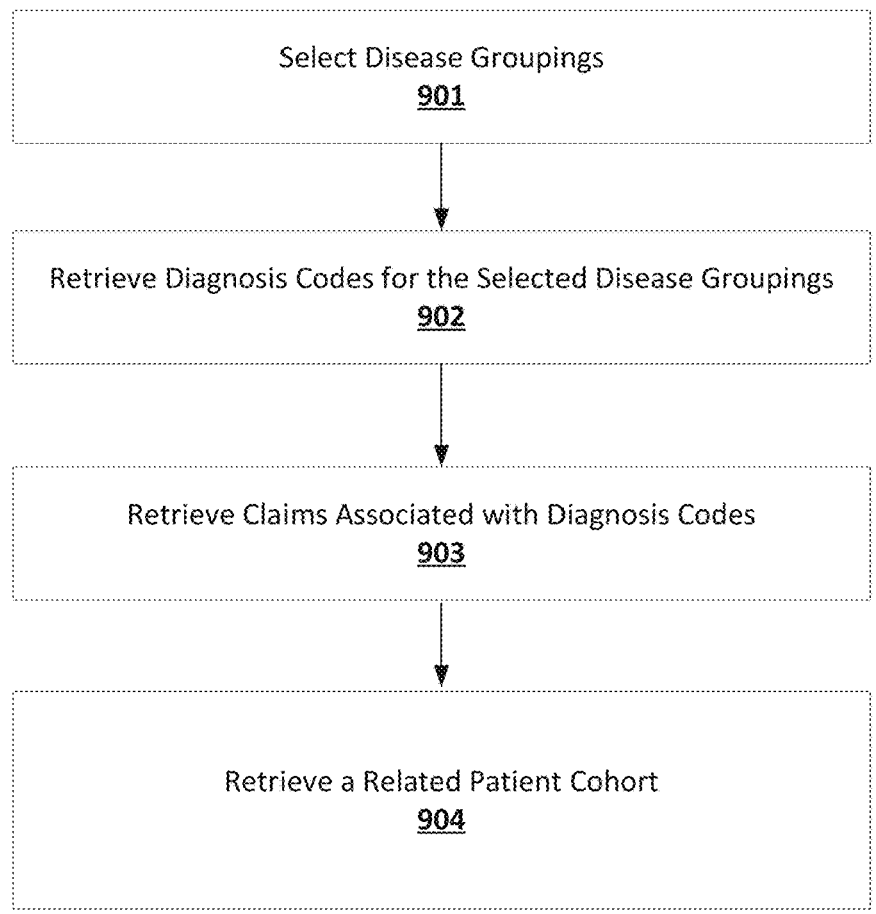

FIG. 9 is an example process for determining a related patient cohort for a primary patient, in accordance with some embodiments discussed herein.

Figure 10:
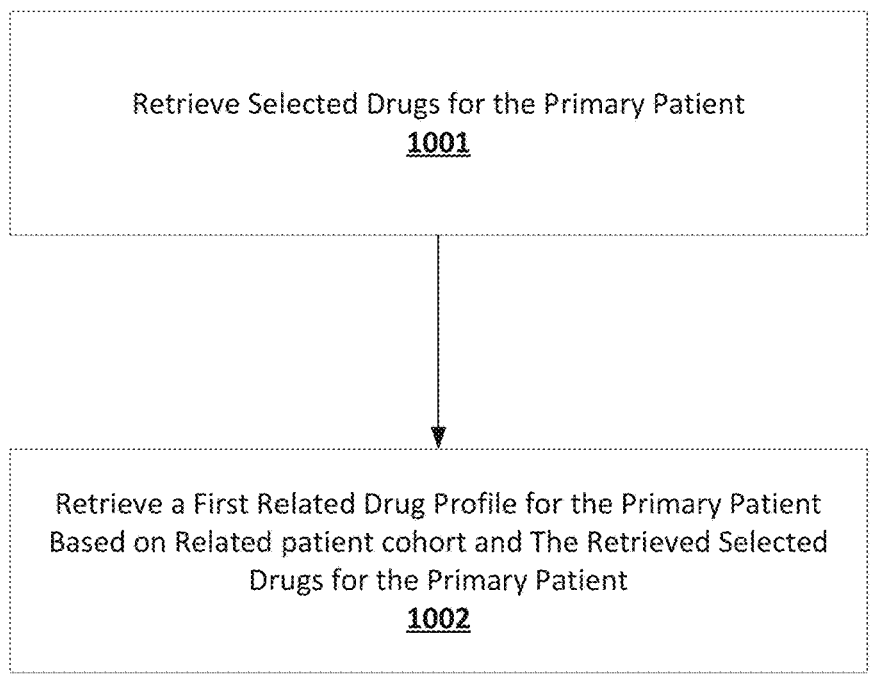

FIG. 10 is an example process for determining a related drug profile for the primary patient, in accordance with some embodiments discussed herein.

Figure 11:
Figure 11:

FIG. 11 is an example process for determining a related primary adverse event occurrence profile for a primary patient, in accordance with some embodiments discussed herein.

Figure 12:
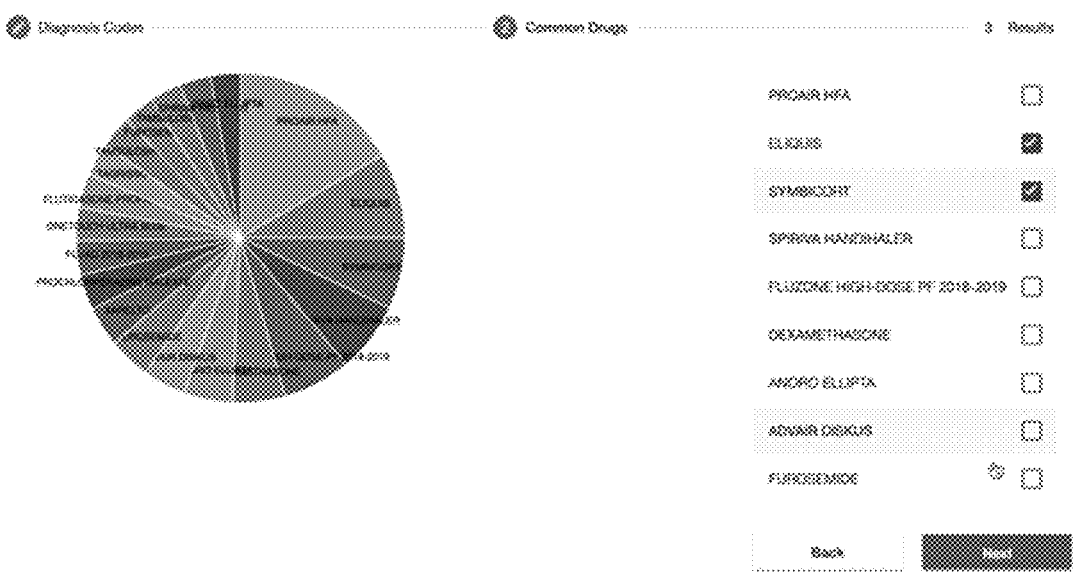

FIG. 12 is an operational example of a drug profile prediction output interface, in accordance with some embodiments.

Figure 13:
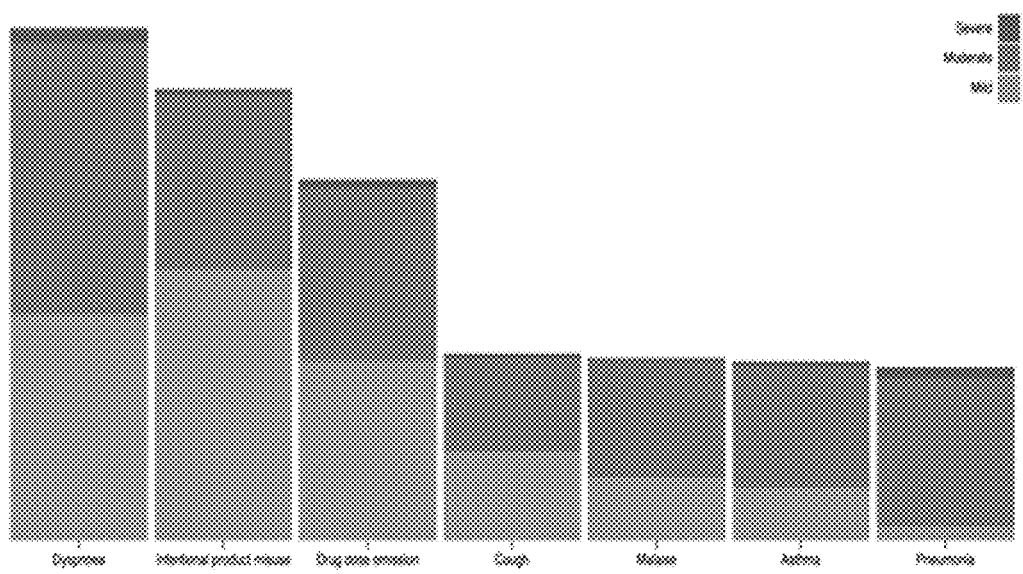

FIG. 13 is an operational example of an adverse account prediction output interface, in accordance with some embodiments.

Figure 14:
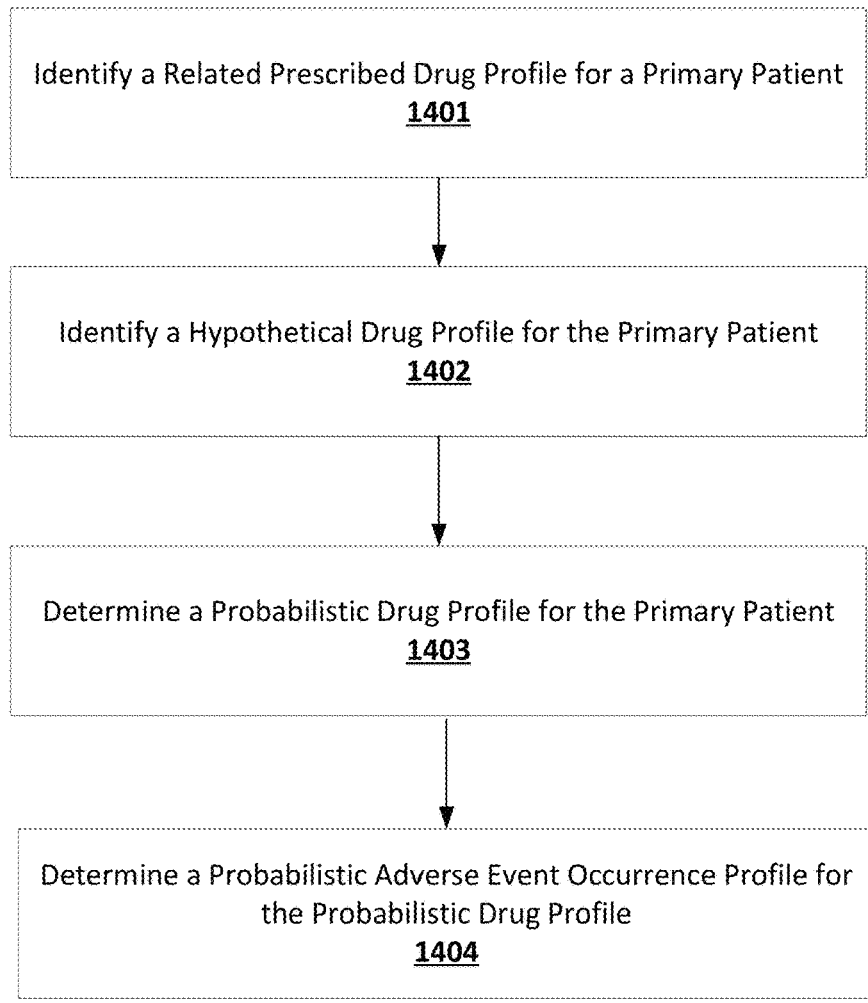

FIG. 14 is an example process for determining a probabilistic adverse event occurrence profile for the probabilistic drug profile, in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview

Various embodiments of the present invention address the problem of predicting adverse consequences of a drug regimen consisting of multiple drugs. Doctors, medical practitioners, and patients do not have the necessary understanding of the side effects and adverse events that may occur when taking a drug regimen consisting of multiple drugs. They rely on existing material such as the package inserts for drugs, as well as commercial online drug resources, such as Micromedex, Up To Date, and Elsevier Gold Standard, to provide any adverse effects information. All these sources, while being accurate in the information they are presenting, are by necessity not precise to a specific patient and/or to a specific drug regimen. This reduces effectiveness and accuracy of adverse effects information provided by the noted traditional source because most patients are taking multiple drugs; thus, presenting statistics on a single drug at a time is not useful. Furthermore, a patient has numerous demographic and clinical factors that can have a significant impact on his likelihood of suffering an adverse event. The published data does not have the ability to take all these factors into consideration. Ideally, a doctor and a patient want to see drug information about patients with similar demographics, similar co-morbid conditions, and a similar list of drugs either already prescribed, or under consideration.

To address the noted technical challenges associated with the side effects and adverse events that may occur when taking a drug regimen consisting of multiple drugs, various embodiments of the present invention disclose performing/executing a graph-based medical prediction for a medical-need scenario. In one aspect, disclosed graph-based medical prediction for a medical-need scenario is utilized to improve validity and accuracy of drug information, and to present a clear picture of the patient's ability to tolerate drug regimens. In some embodiments, a proposed system utilizes one or more patient attribute nodes of a graph-based prediction database to construct what is known as a patient "cohort" which is a set of patients that closely match the primary patient. For example, a patient cohort may be associated with patients having similar demographic features such as age group, race/ethnicity, gender, primary diagnosis, secondary diagnosed conditions, drugs already prescribed, and drugs being considered. By generating the patient cohorts, various embodiments of the present invention enable the doctor to have access to any adverse side effects of the drugs prior to prescribing them. Alternatively, the primary patient can directly access this information.

While various embodiments of the present invention utilize graph-based predictive inference solutions in the context of a drug-adverse-effects predictive inference problem, a person of ordinary skill in the art will recognize that the disclosed techniques can be utilized to perform any predictive task that requires generating predictive inferences across various predictive entities (e.g., patients) and predictive events (e.g., drug prescriptions, adverse effect occurrence events, and/or the like). By utilizing a predictive graph database as a model of a complex (e.g., multi-entity and multi-event) prediction domain which is fed to a graph-based inference model, various embodiments of the present invention provide techniques for simplifying a complex prediction domains in order to provide computationally efficient predictive inferences based at least in part on prediction input data associated with the noted complex prediction domains. By providing the noted techniques for simplifying a complex prediction domains in order to provide computationally efficient predictive inferences based at least in part on the prediction input data associated with the complex prediction domains, various embodiments of the present invention address important technical challenges related to performing predictive inference in complex prediction domains. In doing so, various embodiments of the present invention make important technical contributions to predictive data analysis and improve the effectiveness, the reliability, and the computational efficiency of various existing predictive data analysis systems.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1 is a schematic diagram of an example architecture 100 for performing a graph-based medical prediction for a medical-need scenario. The architecture 100 includes a graph-based medical prediction system 101 that interacts with one or more external computing entities 102. The graph-based medical prediction system 101 may include a graph-based medical prediction computing entity 106 and a storage subsystem 108. The graph-based medical prediction computing entity 106 may be configured to perform graph-based predictive inferences using a graph-based predictive database stored in the storage subsystem 108 and provide graph-based predictive inference outputs corresponding to the graph-based predictive inferences to the external computing entities 102. In some embodiments, upon receiving a prediction request along with the corresponding prediction input data from an external computing entity 102, the graph-based medical prediction computing entity 106 may store such data in its storage subsystem 108 and utilize the stored data in performing graph-based medical predictive inferences.

In some embodiments, the graph-based medical prediction computing entity 106 may communicate with at least one of the external computing entities 102 using one or more communication networks, such as the communication network. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The graph-based medical prediction computing entity 106 includes the storage subsystem 108. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Graph-Based Medical Prediction Computing Entity

FIG. 2 provides a schematic of a graph-based medical prediction computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the graph-based medical prediction computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the graph-based medical prediction computing entity 106 may include or be in communication with one or more processing elements 205 (also referred to as processors, processing circuitry, and/or similar terms used herein interchangeably) that communicate with other elements within the graph-based medical prediction computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the graph-based medical prediction computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the graph-based medical prediction computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the graph-based medical prediction computing entity 106 with the assistance of the processing element 205 and operating system.

As indicated, in one embodiment, the graph-based medical prediction computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the graph-based medical prediction computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the graph-based medical prediction computing entity 106 may include or be in communication with one or more input elements, such as a keyboard input, a mouse input, a touch screen/display input, motion input, movement input, audio input, pointing device input, joystick input, keypad input, and/or the like. The graph-based medical prediction computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the graph-based medical prediction computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the graph-based medical prediction computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MIMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the graph-based medical prediction computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the graph-based medical prediction computing entity 106 and/or various other computing entities.

In another embodiment, the external computing entity 102 may include one or more components or functionality that are the same or similar to those of the graph-based medical prediction computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. Exemplary System Operations

To address the technical challenges associated with the side effects and adverse events that may occur when taking a drug regimen consisting of multiple drugs, various embodiments of the present invention disclose performing/executing a graph-based medical prediction for a medical-need scenario. In one aspect, disclosed graph-based medical prediction for a medical-need scenario is utilized to improve validity and accuracy of drug information, and to present a clear picture of the patient's ability to tolerate drug regimens. In some embodiments, a proposed system utilizes one or more patient attribute nodes of a graph-based prediction database to construct what is known as a patient "cohort" which is a set of patients that closely match the primary patient. For example, a patient cohort may be associated with patients having similar demographic features such as age group, race/ethnicity, gender, primary diagnosis, secondary diagnosed conditions, drugs already prescribed, and drugs being considered. By generating the patient cohorts, various embodiments of the present invention enable the doctor to have access to any adverse side effects of the drugs prior to prescribing them. Alternatively, the primary patient can directly access this information.

While various embodiments of the present invention utilize graph-based predictive inference solutions in the context of a drug-adverse-effects predictive inference problem, a person of ordinary skill in the art will recognize that the disclosed techniques can be utilized to perform any predictive task that requires generating predictive inferences across various predictive entities (e.g., patients) and predictive events (e.g., drug prescriptions, adverse effect occurrence events, and/or the like). By utilizing a predictive graph database as a model of a complex (e.g., multi-entity and multi-event) prediction domain which is fed to a graph-based inference model, various embodiments of the present invention provide techniques for simplifying a complex prediction domains in order to provide computationally efficient predictive inferences based at least in part on prediction input data associated with the noted complex prediction domains. By providing the noted techniques for simplifying a complex prediction domains in order to provide computationally efficient predictive inferences based at least in part on the prediction input data associated with the complex prediction domains, various embodiments of the present invention address important technical challenges related to performing predictive inference in complex prediction domains. In doing so, various embodiments of the present invention make important technical contributions to predictive data analysis and improve the effectiveness, the reliability, and the computational efficiency of various existing predictive data analysis systems.

A. Related Drug Profiles

FIG. 4 provides an example process 400 for performing/executing a graph-based medical prediction for a medical-need scenario associated with the primary patient. Via the various steps/operations of process 400, the graph-based medical prediction computing entity 106 utilizes data associated with a primary patient node of a plurality of patient nodes to, in an efficient and effective manner, perform medical prediction for a medical-need scenario associated with the primary patient and perform prediction-based actions.

The process 400 begins at step/operation 401 when the graph-based medical prediction computing entity 106 determines (e.g., using predictive input data) one or more predictive categories for each patient node of the plurality of patient nodes. In some embodiments, the graph-based medical prediction computing entity 106 determines the predictive categories for each patient based at least in part on patient data stored in a graph-based predictive database, such as the graph-based predictive database 500 of FIG. 5. As depicted in FIG. 5, the graph-based predictive database 500 includes a plurality of patient nodes 502, one or more claim nodes 504, one or more diagnosis code nodes 506, one or more drug nodes 508, and one or more patient attribute nodes 510. As further depicted in FIG. 5, the graph-based predictive database 500 further includes one or more historical relationships 503 between the plurality of patient nodes 502 and the one or more claim nodes 504, one or more encoding relationships 505 between the one or more claim nodes 504 and the one or more diagnosis code nodes 506, one or more intake relationships 507 between the plurality of patient nodes 502 and the one or more drug nodes 508, and one or more adverse event occurrence relationships 509 between the plurality of patients 502 and the one or more drug nodes 508.

In some embodiments, each of the plurality of patient nodes 502 includes information about the plurality of patients. The information may include names of the plurality of patients, social security numbers of the plurality of patients, residential addresses of the plurality of patients, mailing addresses of the plurality of patients, and/or the like. In some embodiments, each of the one or more claim nodes 504 includes one or more previous medical claims of the plurality of patients. In some embodiments, by using a claim node of the primary patient from the one or more claim nodes 504, the graph-based medical prediction computing entity 106 identifies a disease category of the primary patient. In some embodiments, similar diseases are grouped together into a same disease category. As a non-limiting example, "small cell cancer of left lung" and "small cell cancer of right lung" may be grouped together into a same disease category. The determined disease groupings may then be utilized to generate predictive categories, which can in turn be used for purpose of matching patients.

In some embodiments, each of the one or more historical relationships 503 is a path that connects each node of the plurality of patient nodes 502, e.g., each patient, to a respective claim node in the one or more claim nodes 504. Similarly, each of the one or more encoding relationships 505 is a path that connects each node of the one or more claim nodes 504 to a respective diagnosis code node in the one or more diagnosis code nodes 506. In some embodiments, a code is designated to each diagnosed disease. For example, a first code is designated to "small cell cancer of left lung" and a second code is designated to "small cell cancer of right lung." In some embodiments, the one or more diagnosis code nodes 506 may include a code for each candidate diagnosed disease. In some embodiments, the one or more diagnosis code nodes 506 may include a code for each candidate diagnosed disease category. As previously noted, in some embodiments, similar diagnosed diseases with different diagnosis codes are grouped together into a same disease category. Therefore, in some embodiments, an encoding relationship connects a claim node to at least one diagnosis code node. While in some embodiments, a claim includes a diagnosis code, in some embodiments, a claim may include more than one diagnosis codes.

In some embodiments, each of the one or more intake relationships 507 is a path that connects each node of the plurality of patient nodes 502 to a respective drug node in the one or more drug nodes 508. In some embodiments, a drug node includes a drug which is prescribed for a claim of the one or more claim nodes 504 associated with a diagnosed disease of the one or more diagnosis code nodes 506 for a patient of the plurality of patient nodes 502. In some embodiments, a drug node includes more than one drug prescribed for a claim of the one or more claim nodes 504 associated with a diagnosed disease of the one or more diagnosis code nodes 506 for a patient of the plurality of patient nodes 502. In some embodiments, a drug node 508 is associated with one more than one drug.

Referring to FIG. 4 again, at step/operation 402, the graph-based medical prediction computing entity 106 determines a related patient cohort for the primary patient. In some embodiments, the related cohort for the primary patient includes the primary patient node and one or more related patient nodes of the plurality of patient nodes 502 associated with the primary patient node. In some embodiments, the graph-based medical prediction computing entity 106 determines the related patient cohort based at least in part on each of the one or more predictive categories for a patient node of the plurality of patient nodes 502 and each of the one or more patient attribute nodes 510 for a patient node of the plurality of patient nodes 502. In other words, the graph-based medical prediction computing entity 106 identifies a matching population of patients in the plurality of patient nodes 502 based at least in part on the diagnosis code nodes 506, one or more groupings of similar diagnosis code nodes, and the one or more patient attribute nodes 510.

In some embodiments, a plurality of patients' characteristics is used to create the patient cohort. The patient cohort may include a set of patients that closely match the characteristics of the primary patient. To that end, the graph-based medical prediction computing entity 106 may identify patients among the plurality of patient nodes 502 with one or more similar attributes as the primary patient. The one or more patient attribute nodes 510 may include at least one of: an age of the one or more patients of the plurality of patient nodes 502 similar to an age of the primary patient, a race/ethnicity of the one or more patients of the plurality of patient nodes 502 similar to a race/ethnicity of the primary patient, a gender of the one or more patients of the plurality of patient nodes 502 similar to a gender of the primary patient, a primary diagnosis of the one or more patients of the plurality of patient nodes 502 similar to a primary diagnosis of the primary patient, secondary diagnosis conditions of the one or more patients of the plurality of patient nodes 502 similar to secondary diagnosis conditions of the primary patient, one or more drugs prescribed for the one or more patients of the plurality of patient nodes 502 similar to one or more drugs prescribed for the primary patient, and one or more drugs considered for the one or more patients of the plurality of patient nodes 502 similar to one or more drugs being considered for the primary patient.

In some embodiments, step/operation 402 may be performed in accordance with the process depicted in FIG. 9. As depicted in FIG. 9, the corresponding process begins at step/operation 901 when the external computing entity 102 selects disease groupings from a plurality of disease grouping nodes for the primary patient, e.g., using the process depicted in FIG. 8. In some embodiments, the graph-based medical prediction computing entity 106 further selects one or more primary patient's attributes from a plurality of patient attribute nodes. In some embodiments, the graph-based medical prediction computing entity 106 groups one or more similar diseases into a disease grouping.

At step/operation 902, the graph-based medical prediction computing entity 106 retrieves diagnosis codes for the disease groupings selected at step/operation 901. To that end, in some embodiments, the graph-based medical prediction computing entity 106 retrieves one or more pre-loaded disease groupings for diagnosis codes. Alternatively, in some embodiments, the graph-based medical prediction computing entity 106 retrieves diagnosis codes associated with disease groupings. In some embodiments, the diagnosed diseases are categorized into pre-loaded disease groupings. The latter technique may be utilized to categorize recurring diseases or returning primary patients with similar medical conditions and similar diagnoses. It should be noted that, while in some embodiments a claim includes a diagnosis code, in other embodiments a claim may include more than one diagnosis code.

At step/operation 903, the graph-based medical prediction computing entity 106 retrieves claims associated with the diagnosis codes retrieved at step/operation 902. In some embodiments, the graph-based medical prediction computing entity 106 retrieves claims associated with the diagnosis codes based at least in part on the one or more encoding relationships 505 between the one or more claim nodes 504 and the one or more diagnosis code nodes 506.

At step/operation 904, the graph-based medical prediction computing entity 106 retrieves the related patient cohort for the primary patient. In some embodiments, the related cohort for the primary patient includes the primary patient node and one or more related patient nodes of the plurality of patient nodes 502 associated with the primary patient node. The graph-based medical prediction computing entity 106 identifies the related patient cohort, e.g., a cohort that includes a matching population of patients in the plurality of patient nodes 502, based at least in part on the diagnosis code nodes 506, the groupings of similar diagnosis code nodes, and the one or more patient attribute nodes 510.

Returning to FIG. 4, at step/operation 403, the graph-based medical prediction computing entity 106 determines a first related drug profile for the primary patient. The graph-based medical prediction computing entity 106 determines the first related drug profile based at least in part on the one or more intake relationships 507 for each patient node in related patient cohort determined at step/operation 402. In other words, the graph-based medical prediction computing entity 106 identifies one or more common drugs diagnosed for all the patients of the patient cohort. In some embodiments, the determined first related drug profile is prescribed to the primary patient. In some embodiments, the graph-based medical prediction computing entity 106 includes an optional step/operation to add, i.e., blend, one or more additional drugs to the first related drug profile. As a non-limiting example, drugs that are already prescribed for the primary patient can be added to the first related drug profile. As another non-limiting example, drugs that are already prescribed for the primary patient as well as additional drugs that are not part of the first related drug profile can be added to the first related drug profile.

In some embodiments, the graph-based medical prediction computing entity 106 determines a second related drug profile that integrates information about the current drug intake of a primary patient as well as information about the drug intake of a related patient cohort of the primary patient. In such embodiments, the graph-based medical prediction computing entity 106 determines the second related drug profile based at least in part on at least some of the one or more intake relationships 507. In such embodiments, the graph-based medical prediction computing entity 106 determines the second related drug profile based at least in part on one or more current drug intake selections by a requesting external computing entity 102. In some embodiments, external computing entity 102 (e.g., based on end-user input data) selects, or deselects, one or more drugs from the first related drugs profile. As a non-limiting example, the external computing entity 102 may deselect a drug that the primary patient has shown allergic reactions to and exclude that drug from further processing. This exclusion can enhance accuracy of performing the graph-based medical prediction for the medical-need scenario associated with the primary patient by eliminating undesired drugs from the first related drug profile which results in determining the second related drug profile. In some embodiments, the graph-based medical prediction computing entity 106 determines a related prescribed drug profile for the primary patient node based at least in part one or more historical relationships 503 between the primary patient node and one or more claim nodes 504. In some embodiments, the related prescribed drug profile includes drugs already taken by the primary patient. In some embodiments, the graph-based medical prediction computing entity 106 determines the second related drug profile based at least in part on the first related drug profile for the primary patient and the related prescribed drug profile for the primary patient.

In some embodiments, the graph-based medical prediction computing entity 106 determines a probabilistic drug profile for the primary patient profile node based at least in part on a related prescribed drug profile for the primary patient node and a hypothetical drug profile for the primary patient, wherein the related prescribed drug profile comprises drugs already taken by the primary patient; determines a probabilistic adverse consequence prediction based at least in part on the probabilistic drug profile for the primary patient profile given adverse consequence history of the related patient cohort; and generates a second prediction interface based at least in part on the probabilistic adverse consequence predictive inference.

In some embodiments, step/operation 403 may be performed in accordance with the process depicted in FIG. 10, which begins at step/operation 1001 when the graph-based medical prediction computing entity 106 retrieves one or more selected drugs (e.g., one or more prescribed drugs) for the primary patient. The graph-based medical prediction computing entity 106 may retrieve the one or more selected drugs based at least in part on the one or more claims in the one or more claim nodes 504 associated with the primary patient.

At step/operation 1002, the graph-based medical prediction computing entity 106 retrieves a first related drug profile for the primary patient. The graph-based medical prediction computing entity 106 retrieves the first related drug profile based at least in part on the related patient cohort and the one or more selected drugs for the primary patient. In other words, the graph-based medical prediction computing entity 106 identifies one or more drugs commonly diagnosed for all patients of the patient cohort. In some embodiments, the first related drug profile is prescribed for the primary patient. In some embodiments, the graph-based medical prediction computing entity 106 includes an optional step/operation to add one or more additional drugs to the first related drug profile. The one or more additional drugs may include drugs that are already prescribed for the primary patient. In some embodiments, the drugs that are already prescribed for the primary patient and additional drugs that are not part of the first related drug profile, are added to the first related drug profile.

Returning to FIG. 4, at step/operation 404, the graph-based medical prediction computing entity 106 generates a first prediction interface. In some embodiments, the first prediction interface is generated based at least in part on the first related drug profile. In some embodiments, the graph-based medical prediction computing entity 106 generates the first prediction interface with a graph format, which may be built into a user experience. In some embodiments, the graph-based medical prediction computing entity 106 generates the first prediction interface as an interface that may be retrieved using one or more corresponding application program interface (API) calls. In some embodiments, the graph-based medical prediction computing entity 106 generates the first prediction interface as an interface that may be retrieved using one or more corresponding application program interface (API) calls, where the one or more corresponding API calls are integrated into an existing workflow.

In some embodiments, in order to meet privacy or security requirements, the graph-based medical prediction computing entity 106 determines whether the external computing entity 102 is an authorized external computing entity. In some embodiments, the authorized external computing entity is used by an authorized medical practitioner. In some embodiments, the authorized external computing entity is used by the primary patient. In some embodiments, the authorized external computing entity is used by a third-party authorized by the primary patient. In some embodiments, the graph-based medical prediction computing entity 106, upon determining that the external computing entity 102 is an authorized external computing entity, displays the first prediction interface to the external computing entity 102, i.e., to the user.

An operational example of a drug profile prediction output inference 1200 is presented in FIG. 12. As depicted in FIG. 12, the drug profile prediction inference 1200 enables an external computing entity to select or deselect one or more drugs. In some embodiments, the graph-based medical prediction computing entity 106 generates probabilistic drug profiles based on the noted end-user drug selections. As a non-limiting example, the end-user can select one or more drugs in order to cause the graph-based medical prediction computing entity 106 to generate a probabilistic drug profile.

B. Adverse Event Occurrence Profiles

Another challenge for medical practitioners is to accurately determine possible adverse events that may occur when taking a drug regimen consisting of multiple drugs, i.e., side effects of taking various medications. Although adverse event occurrence for a single drug is usually noted on the drug packaging, or otherwise is easy to determine through publicly available databases, this is not the case when more than one drug is prescribed for the patient. In some embodiments, the graph-based medical prediction computing entity 106 generates an adverse event occurrence profile. To generate an adverse event occurrence profile, the graph-based medical prediction computing entity 106 may utilize at least a part of patient data in a graph-based predictive database, such as the graph-based predictive database 500 of FIG.

As depicted in FIG. 5, the graph-based predictive database 500 includes one or more adverse event occurrence relationships 509 between the plurality of patient nodes 502 and the one or more drug nodes 508. An adverse event occurrence relationship is associated with observed side effects of a particular drug of the one or more drug nodes 508 which is prescribed for a particular patient of the plurality of patient nodes 502. In some embodiments, each of the one or more adverse event occurrence relationships 509 is associated with observed rates of particular side effects and particular adverse events encountered in the real world, for patients that match the primary patient on demographics and diagnoses, i.e., members of the patient cohort, who are taking a similar set of prescribed drugs. In some embodiments, the graph-based medical prediction computing entity 106 determines the one or more adverse event occurrence relationships 509 based at least in part on the Food and Drug Administration (FDA) Adverse Event Reporting System (FAERS). In some embodiments, the graph-based medical prediction computing entity 106 determines the one or more adverse event occurrence relationships 509 based at least in part on one or more existing adverse event occurrences in the one or more claim nodes 504. In some embodiments, by using the one or more adverse event occurrence relationships 509 based at least in part on the FAERS and the one or more claim nodes 504, the graph-based medical prediction computing entity 106 determines a related adverse event occurrence profile.

FIG. 6 is an operational flow diagram of an example process 600 for determining a related adverse event occurrence profile, according to some embodiments. In some embodiments, the graph-based medical prediction computing entity 106 retrieves the primary patient 602 and determines one or more predictive categories 604 for each patient node of the plurality of patient nodes. In some embodiments, the graph-based medical prediction computing entity 106 determines the related patient cohort 606 for the primary patient 602. In some embodiments, the related patient cohort 606 for the primary patient 602 includes the primary patient node and one or more related patient nodes of the plurality of patient nodes associated with the primary patient node. In some embodiments, the graph-based medical prediction computing entity 106 determines the related patient cohort 606 based at least in part on each one or more predictive categories for a patient node of the plurality of patient nodes and each one or more patient attribute nodes for a patient node of the plurality of patient nodes. In some embodiments, the graph-based medical prediction computing entity 106 determines the related adverse event occurrence profile 608 based at least in part on the one or more adverse event occurrence relationships for each of the one or more drug nodes in the first related drug profile.

In some embodiments, the graph-based medical prediction computing entity 106 generates a second prediction interface based at least in part on the related adverse event occurrence profile. In some embodiments, the graph-based medical prediction computing entity 106 generates the second prediction interface with a graph format which is built into a user experience. In some embodiments, the graph-based medical prediction computing entity 106 generates the second prediction interface as an interface that may be retrieved using one or more corresponding API calls. In some embodiments, the graph-based medical prediction computing entity 106 generates the second prediction interface as an interface that may be retrieved using one or more API calls, where the one or more API calls are integrated into an existing workflow. In some embodiments, the one or more adverse event occurrence relationships 509 are determined based at least in part on the one or more claim nodes 504. In some embodiments, the one or more adverse event occurrence relationships 509 are determined based at least in part on one or more adverse nodes. In some embodiments, the one or more adverse nodes includes data obtained from an adverse event reporting system such as FDA's FAERS.

FIG. 11 is an example process 1100 for performing/executing a graph-based prediction in order to generate a related primary adverse event occurrence profile, in accordance with some embodiments. At step/operation 1101, the external computing entity 102 selects drugs based at least in part on the related patient cohort and the one or more prescribed drugs for the primary patient retrieved at step/operation 1004.

At step/operation 1102, the graph-based medical prediction computing entity 106 retrieves the first adverse event occurrence profile from a source. In some embodiments, the source includes the FAERS. Alternatively, the graph-based medical prediction computing entity 106 retrieves the first adverse event occurrence from one or more existing adverse event occurrences in the one or more claim nodes 504.

At step/operation 1103, the graph-based medical prediction computing entity 106 determines the related primary adverse event occurrence profile. The related adverse event occurrence profile is determines based at least in part on the first adverse event occurrence profile retrieved at step/operation 1102. In some embodiments, the graph-based medical prediction computing entity 106 generates a third prediction interface based at least in part on the related adverse event occurrence profile and the related primary adverse event occurrence profile. In some embodiments, the one or more adverse event occurrence relationships 509 and the one or more primary adverse event occurrence relationships are determined based at least in part on the one or more claim nodes 504. In some embodiments, the one or more adverse event occurrence relationships 509 and the one or more primary adverse event occurrence relationships are determined based at least in part on one or more adverse event occurrence nodes. The one or more adverse event occurrence nodes include data obtained from FAERS.

An operational example of an adverse event profile prediction output inference 1300 is presented in FIG. 13. As an example, when a regimen of three drugs is prescribed for the primary patient, and each drug carries a specific risk of one or more adverse event occurrences for the patient cohort, then the graph-based medical prediction computing entity 106 determines the risk of each adverse event occurrences for each drug for the primary patient. The exemplary adverse event profile prediction output inference 1300 of FIG. 13 depicts the adverse event occurrence qualitatively, e.g., mild, moderate and severe. Alternatively, in some embodiments, the first prediction interface displays the adverse event occurrence quantitatively, e.g., 25% possibility of severe headache for a specific drug of the related drug profile.

C. Per-Patient Disease Grouping Detection

Since each disease is designated a specific disease code, similar diseases may need to be grouped together to improve the accuracy of the performing graph-based medical prediction. For example, malignant neoplasm of right lung lobe and malignant neoplasm of left lung lobe are similar diseases with identically prescribed drugs. Therefore, in some embodiments, similar diseases and medical conditions with identical diagnoses are grouped together into a single disease groups. FIG. 7 provides an example process 700 for determining one or more diagnosis groupings for the primary patient, according to some embodiments. The determined disease groupings can be used to determine predictive categories for a patient at step/operation 401 of process 400 depicted in FIG. 4.

The process 700 begins at step/operation 701 when the graph-based medical prediction computing entity 106 enables the external computing entity 102 to choose the primary patient. The primary patient can be chosen from a plurality of patient nodes 502. At step/operation 702, the graph-based predictive computing entity 106 retrieves one or more claim nodes associated with the primary patient chosen at step/operation 701. In some embodiments, the one or more claim nodes 502 includes one or more previous medical claims associated with the primary patient.

At step/operation 703, the graph-based medical prediction computing entity 106 retrieves one or more diagnosis code nodes 506 associated with the one or more claim nodes 504. In some embodiments, the one or more claim nodes 504 includes one or more previous medical claims of the plurality of patients. In some embodiments, by using a retrieved claim node of the primary patient from the one or more claim nodes 504, the graph-based medical prediction computing entity 106 identifies one or more disease categories for the primary patient. In some embodiments, the graph-based medical prediction computing entity 106 utilizes the determined one or more disease categories to generate per-patient predictive categories at step/operation 401.

At step/operation 704, the graph-based medical prediction computing entity 106 retrieves one or more pre-loaded disease groupings for diagnosis codes, where each pre-loaded disease grouping is associated with a group of diagnosis codes. At step/operation 705, the graph-based medical prediction computing entity 106 determines the disease groupings for the patient by selecting preloaded groupings associated with the diagnosis codes retrieved at step/operation 703.

FIG. 8 is an operational example of a graph-based medical prediction for a medical-need scenario associated with a primary patient. The operational example includes the primary patient node information in its first column, one or more diagnosis code node information in its second column, groupings of the one or more diagnosis codes in its third column, and indications of whether each of the groupings is selected for analysis in its fourth code. The primary patient node information includes patient's information, e.g., name, gender, age, and race. The diagnosis code node information includes one or more diagnosis code, e.g., malignant neoplasm of right lung lobe, malignant neoplasm of left lung lobe, elevated blood pressure, and fracture of right ulna.

As depicted in the operational example of FIG. 8, two of the diagnosis codes, e.g., malignant neoplasm of right lung lobe and malignant neoplasm of left lung lobe, are grouped together into a grouping of diagnosis codes, e.g., lung cancer. The grouping includes similar diagnosed diseases. The malignant neoplasm of the right lung lobe, malignant neoplasm of left lung lobe and the elevated blood pressure are further chosen for further analysis. The analysis may include determining the first related drug profile and the related adverse event occurrence profile.

D. Probabilistic Adverse Event Occurrence Profiles

In some embodiments, the graph-based medical prediction computing entity 106 may be configured to perform probabilistic inferences using hypothetical predictive factors. A probabilistic inference is an inference that seeks to identify events (e.g., adverse consequences) likely to occur as a result of adding a hypothetical set of predictive factors (e.g., a hypothetical drug profile) to a currently active set of predictive factors (e.g., a current prescribed drug profile). An example of a probabilistic inference is a what-if inference seeking to identify changes in adverse consequences of a prescribed drug regimen likely to come about a result of adding new drugs to the drug regimen.

FIG. 14 is a flowchart diagram of an example process 1400 for determining probabilistic adverse event occurrence profiles. While the exemplary process 1400 is described with respect to probabilistic drug-related predictions, a person of ordinary skill in the relevant technology will recognize that the disclosed techniques can be extended to other probabilistic prediction tasks, e.g., financial prediction tasks seeking to probabilistically identify likely investment outcomes resulting from hypothetical changes in investment portfolios.

The process 1400 begins at step/operation 1401 when the graph-based medical prediction computing entity 106 identifies a related prescribed drug profile for a primary patient. In some embodiments, the related prescribed drug profile for a primary patient includes an indication of at least a subset (e.g., a relevant subset, a critical subset, an adverse-event-prone subset, and/or the like) of a set of drugs currently prescribed by the primary patient. In some embodiments, the related prescribed drug profile for a primary patient includes an indication of at least a subset (e.g., a relevant subset, a critical subset, an adverse-event-prone subset, and/or the like) of a set of drugs currently being consumed by the primary patient as determined by one or more pharmacy-related medical claims of the primary patient.

At step/operation 1402, the graph-based medical prediction computing entity 106 identifies a hypothetical drug profile for the primary patient. In some embodiments, the graph-based medical prediction computing entity 106 determines the hypothetical drug profile for the primary patient based on a medical provider input. In some embodiments, the graph-based medical prediction computing entity 106 determines the hypothetical drug profile for the primary patient based on detecting introduction of a new drug in a real-time drug marketing database. In some embodiments, the graph-based medical prediction computing entity 106 determines the hypothetical drug profile for the primary patient based on patient drug selections.

At step/operation 1403, the graph-based medical prediction computing entity 106 determines a probabilistic drug profile for the primary patient based on the related prescribed drug profile for the primary patient identified in step/operation 1401 and the hypothetical drug profile for the primary patient identified in step/operation 1402. In some embodiments, the graph-based medical prediction computing entity 106 determines the probabilistic drug profile for the primary patient by combining each unique drug from the related prescribed drug profile for the primary patient identified in step/operation 1401 and the hypothetical drug profile for the primary patient identified in step/operation 1402. In some embodiments, the graph-based medical prediction computing entity 106 determines the probabilistic drug profile for the primary patient by selecting, from each medical condition associated with the primary patient, a selected drug from either or both of the related prescribed drug profile for the primary patient identified in step/operation 1401 and the hypothetical drug profile for the primary patient identified in step/operation 1402.

At step/operation 1404, the graph-based medical prediction computing entity 106 determines a probabilistic adverse event occurrence profile for the probabilistic drug profile. In some embodiments, the graph-based medical prediction computing entity 106 determines the probabilistic adverse event occurrence profile for the probabilistic drug profile using the techniques described in relation to step/operation 1103 of FIG. 11. In some embodiments, the graph-based medical prediction computing entity 106 determines the probabilistic adverse event occurrence profile for the probabilistic drug profile using a stochastic predictive inference model that includes a stochastic factor to adjust the weight ascribed to each drug in the hypothetical drug profile for the primary patient identified in step/operation 1402. In some embodiments, the graph-based medical prediction computing entity 106 determines the probabilistic adverse event occurrence profile for the probabilistic drug profile using a machine learning model, such as a neural network machine learning model.

In some embodiments, the graph-based medical prediction computing entity 106 utilizes at least one of the drug profiles and/or the adverse event occurrence profiles introduced herein to perform one or more prediction-related actions. For example, the graph-based medical prediction computing entity 106 may utilize the drug profiles and/or the adverse event occurrence profiles introduced herein to automatically schedule medical appointments, generate practitioner reminders, generate patient reminders, automatically generate prescriptions, and/or the like.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for performing a graph-based medical prediction for a medical-need scenario associated with a primary patient, the computer-implemented method comprising:
   generating, by one or more processors, a graph model for a prediction domain, wherein:
   (i) the graph model comprises a plurality of nodes and a plurality of node paths that connect one or more of the plurality of nodes,
   (ii) the plurality of nodes comprises a plurality of patient nodes, one or more claim nodes, one or more diagnosis nodes, one or more drug nodes, and one or more patient attribute nodes,
   (iii) the plurality of node paths is indicative of one or more relationships among the plurality of nodes,
   (iv) the one or more relationships comprise: (a) one or more intake relationships connecting one or more of the plurality of patient nodes and one or more of the one or more drug nodes and (b) one or more adverse event occurrence relationships connecting one or more of the plurality of patient nodes and the one or more drug nodes, and
   (v) an adverse event occurrence relationship identifies an observed side effect of a particular drug of the one or more drug nodes for a particular patient node of the plurality of patient nodes;
   generating, by the one or more processors and for the graph model, based at least in part on the one or more patient attribute nodes, a related patient cohort for a primary patient node, wherein the related patient cohort comprises the primary patient node and one or more related patient nodes associated with the primary patient node;
   determining, by the one or more processors and based at least in part on the one or more intake relationships, a first related drug profile for the primary patient node, wherein the first related drug profile identifies one or more common drugs associated with the primary patient node and the one or more related patient nodes;
   generating, by the one or more processors, a drug profile prediction interface based at least in part on the first related drug profile, wherein the drug profile prediction interface comprises a first probabilistic drug profile for the primary patient node;
   providing, by the one or more processors and for display, the drug profile prediction interface to a user, wherein the drug profile prediction interface comprises a plurality of interactive drug icons, each corresponding to a respective drug node of the one or more drug nodes in the graph model; and
   in response to user input indicative of a selection or deselection of at least one of the plurality of interactive drug icons;
      generating, by the one or more processors, a hypothetical drug profile for the primary patient node based at least in part on the first probabilistic drug profile and the user input, wherein the hypothetical drug profile comprises a second probabilistic drug profile for the primary patient node; and
      generating, by the one or more processors and using a machine learning model and the graph model, a probabilistic adverse event occurrence profile for the second probabilistic drug profile based at least in part on the one or more adverse event occurrence relationships.

2. The computer-implemented method of claim 1 further comprising:
   determining, based at least in part on the one or more adverse event occurrence relationships for each of the one or more drug nodes in the first related drug profile, a related adverse event occurrence profile; and
   generating a second prediction interface based at least in part on the related adverse event occurrence profile.

3. The computer-implemented method of claim 1, wherein the one or more adverse event occurrence relationships are determined based at least in part on one of: the one or more claim nodes, and one or more adverse nodes, wherein the one or more adverse nodes comprise data obtained from an adverse event reporting system.

4. The computer-implemented method of claim 1, wherein providing for display the drug profile prediction interface to the user further comprises:
   determining whether the user is an authorized user, wherein the authorized user is at least one of: an authorized medical practitioner, the primary patient, or a third-party authorized by the primary patient; and
   providing for display the drug profile prediction interface to the user in response to a determination that the user is the authorized user.

5. The computer-implemented method of claim 1, wherein the one or more patient attribute nodes comprises at least one of: an age of one or more patient nodes of the plurality of patient nodes similar to an age of the primary patient, a race/ethnicity of the one or more patient nodes similar to a race/ethnicity of the primary patient, a gender of the one or more patients of the plurality of patient nodes similar to a gender of the primary patient, a primary diagnosis of the one or more patient nodes similar to a primary diagnosis of the primary patient, secondary diagnosis conditions of the one or more patient nodes similar to secondary diagnosis conditions of the primary patient, one or more drugs prescribed for the one or more patient nodes similar to one or more drugs prescribed for the primary patient, and one or more drugs considered for the one or more patient nodes similar to one or more drugs being considered for the primary patient.

6. The computer-implemented method of claim 1, wherein the one or more relationships comprise one or more historical relationships connecting one or more of the plurality of patient nodes and the one or more claim nodes, and wherein the computer-implemented method further comprises:
   determining, based at least in part on the one or more historical relationships between the primary patient node and the one or more claim nodes, a related prescribed drug profile for the primary patient node, wherein the related prescribed drug profile comprises drugs already taken by the primary patient;
   determining, based at least in part on the first related drug profile for the primary patient node and the related prescribed drug profile for the primary patient, a second related drug profile; and
   generating a second drug profile prediction interface based at least in part on the second related drug profile.

7. The computer-implemented method of claim 6, further comprising:
   determining, based at least in part on the one or more intake relationships for at least one patient node in the related patient cohort and the primary patient node, the second related drug profile for the primary patient node; and generating the second drug profile prediction interface based at least in part on the second related drug profile.

8. The computer-implemented method of claim 6, further comprising:

determining whether the user is an authorized user, wherein the authorized user is at least one of: an authorized medical practitioner, the primary patient, or a third-party authorized by the primary patient; and providing for display the second drug profile prediction interface to the user in response to a determination that the user is the authorized user.

9. The computer-implemented method of claim 1, wherein the one or more adverse event occurrence relationships are determined based at least in part on data obtained from an adverse event reporting system.

10. An apparatus for performing a graph-based medical prediction for a medical-need scenario associated with a primary patient node, the apparatus comprising one or more processors and at least one memory including program code, the at least one memory and the program code configured to, with the one or more processors, cause the apparatus to at least:

generate a graph model for a prediction domain, wherein:
(i) the graph model comprises a plurality of nodes and a plurality of node paths that connect one or more of the plurality of nodes,
(ii) the plurality of nodes comprises a plurality of patient nodes, one or more claim nodes, one or more diagnosis nodes, one or more drug nodes, and one or more patient attribute nodes,
(iii) the plurality of node paths is indicative of one or more relationships among the plurality of nodes,
(iv) the one or more relationships comprise: (a) one or more intake relationships connecting one or more of the plurality of patient nodes and one or more of the one or more drug nodes and (b) one or more adverse event occurrence relationships connecting one or more of the plurality of patient nodes and the one or more drug nodes, and
(v) an adverse event occurrence relationship identifies an observed side effect of a particular drug of the one or more drug nodes for a particular patient node of the plurality of patient nodes;

generate for the graph model, based at least in part on the one or more patient attribute nodes, a related patient cohort for the primary patient node, wherein the related patient cohort comprises the primary patient node and one or more related patient nodes associated with the primary patient node;

determine, based at least in part on the one or more intake relationships, a first related drug profile for the primary patient node, wherein the first related drug profile identifies one or more common drugs associated with the primary patient node and the one or more related patient nodes;

generate a drug profile prediction interface based at least in part on the first related drug profile, wherein the drug profile prediction interface comprises a first probabilistic drug profile for the primary patient node;

providing for display the drug profile prediction interface to a user, wherein the drug profile prediction interface comprises a plurality of interactive drug icons, each corresponding to a respective drug node of the one or more drug nodes in the graph model; and in response to user input indicative of a selection or deselection of at least one of the plurality of interactive drug icons:

generate a hypothetical drug profile for the primary patient node based at least in part on the first probabilistic drug profile and the user input, wherein the hypothetical drug profile comprises a second probabilistic drug profile for the primary patient node; and generate, using a machine learning model and the graph model, a probabilistic adverse event occurrence profile for the second probabilistic drug profile based at least in part on the one or more adverse event occurrence relationships.

11. The apparatus of claim 10, wherein the one or more patient attribute nodes comprises at least one of: an age of one or more patient nodes of the plurality of patient nodes similar to an age of a primary patient corresponding to the primary patient node, a race/ethnicity of the one or more patient nodes similar to a race/ethnicity of the primary patient, a gender of the one or more patient nodes similar to a gender of the primary patient, a primary diagnosis of the one or more patient nodes similar to a primary diagnosis of the primary patient, secondary diagnosis conditions of the one or more patient nodes similar to secondary diagnosis conditions of the primary patient, one or more drugs prescribed for the one or more patient nodes similar to one or more drugs prescribed for the primary patient, and one or more drugs being considered for the one or more patient nodes similar to one or more drugs being considered for the primary patient.

12. The apparatus of claim 11, wherein the at least one memory and the program code are further configured to, with the one or more processors, cause the apparatus to at least:

determine whether the user is an authorized user, wherein the authorized user is at least one of: an authorized medical practitioner, a primary patient, or a third-party authorized by the primary patient; and provide for display the drug profile prediction interface to the user responsive to a determination that the user is the authorized user.

13. The apparatus of claim 11, wherein the one or more relationships comprise one or more historical relationships connecting one or more of the plurality of patient nodes and the one or more claim nodes, and wherein the at least one memory and the program code are further configured to, with the one or more processors, cause the apparatus to at least:

determine, based at least in part on the one or more historical relationships between the primary patient node and the one or more claim nodes, a related prescribed drug profile for the primary patient node, wherein the related prescribed drug profile comprises drugs already taken by the primary patient;

determine, based at least in part on the first related drug profile for the primary patient node and the related prescribed drug profile for the primary patient node, a second related drug profile; and generate a second drug profile prediction interface based at least in part on the second related drug profile.

14. A computer program product for performing a graph-based medical prediction for a medical-need scenario associated with a primary patient node, the computer program product comprising at least one non-transitory computer-readable storage medium having computer-readable program code portions stored therein, the computer-readable program code portions configured to:

generating a graph model for a prediction domain, wherein:
  (i) the graph model comprises a plurality of nodes and a plurality of node paths that connect one or more of the plurality of nodes,
  (ii) the plurality of nodes comprises a plurality of patient nodes, one or more claim nodes, one or more diagnosis nodes, one or more drug nodes, and one or more patient attribute nodes,
  (iii) the plurality of node paths is indicative of one or more relationships among the plurality of nodes,
  (iv) the one or more relationships comprise: (a) one or more intake relationships connecting one or more of the plurality of patient nodes and one or more of the one or more drug nodes and (b) one or more adverse event occurrence relationships connecting one or more of the plurality of patient nodes and the one or more drug nodes, and
  (v) an adverse event occurrence relationship identifies an observed side effect of a particular drug of the one or more drug nodes for a particular patient node of the plurality of patient nodes;
generating for the graph model, based at least in part on the one or more patient attribute nodes, a related patient cohort for the primary patient node, wherein the related patient cohort comprises the primary patient node and one or more related patient nodes associated with the primary patient node;
determine, based at least in part on the one or more intake relationships, a first related drug profile for the primary patient node, wherein the first related drug profile identifies one or more common drugs associated with the primary patient node and the one or more related patient nodes;
generate a drug profile prediction interface based at least in part on the first related drug profile, wherein the drug profile prediction interface comprises a first probabilistic drug profile for the primary patient node;
providing for display the drug profile prediction interface to a user, wherein the drug profile prediction interface comprises a plurality of interactive drug icons, each corresponding to a respective drug node of the one or more drug nodes in the graph model; and
in response to user input indicative of a selection or deselection of at least one of the plurality of interactive drug icons:
  generating a hypothetical drug profile for the primary patient node based at least in part on the first probabilistic drug profile and the user input, wherein the hypothetical drug profile comprises a second probabilistic drug profile for the primary patient node; and
  generating, using a machine learning model and the graph model, a probabilistic adverse event occurrence profile for the second probabilistic drug profile based at least in part on the one or more adverse event occurrence relationships.

15. The computer program product of claim 14, wherein the one or more patient attribute nodes comprises at least one of: an age of one or more patient nodes of the plurality of patient nodes similar to an age of the primary patient node, a race/ethnicity of the one or more patient nodes similar to a race/ethnicity of the primary patient node, a gender of the one or more patient nodes similar to a gender of the primary patient node, a primary diagnosis of the one or more patient nodes similar to a primary diagnosis of the primary patient node, secondary diagnosis conditions of the one or more patient nodes similar to secondary diagnosis conditions of the primary patient node, one or more drugs prescribed for the one or more patient nodes similar to one or more drugs prescribed for the primary patient node, and one or more drugs being considered for the one or more patient nodes similar to one or more drugs being considered for the primary patient node.

16. The computer program product of claim 15, wherein the computer-readable program code portions are further configured to:
  determine whether the user is an authorized user, wherein the authorized user is at least one of: an authorized medical practitioner, a primary patient corresponding to the primary patient node, or a third-party authorized by the primary patient; and
  provide for display the drug profile prediction interface to the user responsive to a determination that the user is the authorized user.

17. The computer-implemented method of claim 1, wherein the computer-implemented method further comprises:
  providing for display a probabilistic adverse event occurrence interface to the user, wherein the probabilistic adverse event occurrence interface comprises the probabilistic adverse event occurrence profile.

* * * * *

UNITED STATES PATENT AND TRADEMARK OFFICE
CERTIFICATE OF CORRECTION

PATENT NO. : 11,763,946 B2
APPLICATION NO. : 16/803465
DATED : September 19, 2023
INVENTOR(S) : Mark Gregory Megerian et al.

It is certified that error appears in the above-identified patent and that said Letters Patent is hereby corrected as shown below:

In the Claims

In Column 23, Line 58, Claim 1, delete "drug icons;" and insert -- drug icons: --, therefor.

In Column 24, Line 35, Claim 5, delete "more patients of the plurality of" and insert -- more --, therefor.

Signed and Sealed this
Twelfth Day of December, 2023

*Katherine Kelly Vidal*

Katherine Kelly Vidal
*Director of the United States Patent and Trademark Office*